(12) United States Patent
Weiss et al.

(10) Patent No.: US 11,865,515 B2
(45) Date of Patent: Jan. 9, 2024

(54) CATALYST FOR OLEFINS GENERATION

(71) Applicant: ExxonMobil Technology and Engineering Company, Annandale, NJ (US)

(72) Inventors: Brian M. Weiss, Bridgewater, NJ (US); Sophie Liu, Hampton, NJ (US); Joseph M. Falkowski, Hampton, NJ (US); Marc R. Schreier, Nazareth, PA (US); Herb W. Barry, Yardville, PA (US)

(73) Assignee: EXXONMOBIL TECHNOLOGY AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 17/457,677

(22) Filed: Dec. 6, 2021

(65) Prior Publication Data

US 2023/0173463 A1  Jun. 8, 2023

(51) Int. Cl.
*B01J 21/04* (2006.01)
*B01J 21/10* (2006.01)
*B01J 23/00* (2006.01)
*B01J 23/02* (2006.01)
*B01J 23/10* (2006.01)
(Continued)

(52) U.S. Cl.
CPC ............. *B01J 23/32* (2013.01); *B01J 23/002* (2013.01); *B01J 23/005* (2013.01); *B01J 23/02* (2013.01); *B01J 23/30* (2013.01); *B01J 37/0215* (2013.01); *C07C 5/3332* (2013.01); *B01J 21/04* (2013.01); *B01J 21/10* (2013.01); *B01J 2523/12* (2013.01); *B01J 2523/22* (2013.01); *B01J 2523/31* (2013.01); *B01J 2523/69* (2013.01); *B01J 2523/72* (2013.01); *C07C 2523/02* (2013.01); *C07C 2523/30* (2013.01); *C07C 2523/32* (2013.01)

(58) Field of Classification Search
CPC . B01J 21/04; B01J 21/10; B01J 23/002; B01J 23/005; B01J 23/02; B01J 23/10; B01J 23/30; B01J 23/32; B01J 23/34; B01J 37/0215; C07C 5/3332
USPC ........ 502/300, 302–304, 324, 349–351, 355, 502/415, 439
See application file for complete search history.

(56) References Cited

U.S. PATENT DOCUMENTS 3,894,965 A * 7/1975 Foster ...................... B01J 35/04
502/313
4,368,029 A * 1/1983 Lacroix ................ B01J 23/8993
431/328

(Continued)

FOREIGN PATENT DOCUMENTS

WO  2021025942 A1  2/2021

*Primary Examiner* — Cam N. Nguyen
(74) *Attorney, Agent, or Firm* — SHOOK, HARDY & BACON L.L.P.

(57) ABSTRACT

An active material useful in an oxidative dehydrogenation reactor system has an active phase, and a mixed metal oxide support phase. The active phase includes a transition metal oxide such as manganese oxide, which is reversibly oxidizable and/or reducible between oxidized and reduced states. The support phase includes a mixed metal oxide of a two or more IUPAC Group 2-14 elements. The active phase can also include a promoter such as Na-WO4 and/or a selectivity modifier such as Al or ceria. Also, a reactor including the active material in a reactor, a method of making the active material, and a method of using the active material in a regenerative reaction process.

17 Claims, 9 Drawing Sheets

(51) Int. Cl.
   *B01J 23/30* (2006.01)
   *B01J 23/32* (2006.01)
   *B01J 23/34* (2006.01)
   *B01J 37/02* (2006.01)
   *C07C 5/333* (2006.01)

(56) References Cited

U.S. PATENT DOCUMENTS

| | | | | |
|---|---|---|---|---|
| 4,929,586 A * | 5/1990 | Hegedus | ............ | B01D 53/8628 |
| | | | | 502/247 |
| 4,975,256 A * | 12/1990 | Hegedus | ................ | B01J 35/002 |
| | | | | 423/239.1 |
| 5,137,855 A * | 8/1992 | Hegedus | ............. | B01J 35/0026 |
| | | | | 502/309 |
| 7,977,274 B2 * | 7/2011 | Gueckel | ............... | C07D 303/04 |
| | | | | 502/64 |
| 8,143,186 B2 * | 3/2012 | Rytter | ................... | C10G 2/332 |
| | | | | 502/328 |
| 8,722,001 B2 * | 5/2014 | Ono | ........................ | F01N 13/16 |
| | | | | 502/328 |
| 9,394,214 B2 | 7/2016 | Henao et al. | | |
| 9,399,605 B2 | 7/2016 | Henao et al. | | |
| 9,669,395 B2 * | 6/2017 | Hung | ................... | B01J 37/0205 |
| 10,087,122 B2 * | 10/2018 | Fang | ...................... | B01J 29/405 |
| 10,828,621 B2 * | 11/2020 | Bunquin | .................. | B01J 23/34 |
| 11,000,832 B1 * | 5/2021 | Do | ........................ | B01J 37/0063 |
| 2008/0261090 A1 * | 10/2008 | Benito Gonzalez | ... | B01J 21/066 |
| | | | | 252/373 |
| 2012/0028794 A1 * | 2/2012 | Lam | ....................... | B01J 35/065 |
| | | | | 502/325 |
| 2012/0149559 A1 * | 6/2012 | Wolan | .................... | C10G 2/331 |
| | | | | 502/319 |
| 2013/0244869 A1 * | 9/2013 | Auer | ....................... | C01G 31/02 |
| | | | | 502/309 |
| 2017/0106352 A1 * | 4/2017 | Sharma | .................. | C10G 11/04 |
| 2019/0055178 A1 | 2/2019 | Weiss et al. | | |

* cited by examiner

CATALYST FOR OLEFINS GENERATION

FIELD

This disclosure relates to active materials, processes for making the same, reactors comprising the same, and use thereof. In particular, this disclosure relates to active materials comprising a transition metal element and a support, reactors comprising the same, processes for making the same, and use thereof. This disclosure is useful, e.g., in converting alkanes to form olefins.

BACKGROUND

The oxydehydrogenation of alkanes to form olefins in a reverse flow reactor (RFR) using an oxygen transfer agent (OTA) is known from patent document US 2019/0055178 A1. This reference discloses various OTAs based on manganese or manganese composites, including $Mn_2O_3$ on silica or quartz, $Mn_2O_3$ on $MnTiO_3$, $CaMnO_3$, $Mn_3O_4/Na_2WO_4/MnWO_4$, etc. Similarly, patent documents U.S. Pat. Nos. 9,394,214 and 9,399,605, both of which are incorporated herein by reference in their entireties, disclose the use of oxygen storage media such as perovskites and perovskite-like materials in chemical looping RFRs to oxidatively couple methane molecules to form longer-chained hydrocarbons.

In prior art, ethane, naphtha or other hydrocarbon is converted to ethylene by thermal pyrolysis in the steam cracking process. Pyrolysis occurs at high temperature (750-900° C.), low pressure (15-25 psig), and short residence time (0.1-0.4 seconds above 600-700° C.). The process consumes significant heat. This heat is usually supplied by a fired furnaces. Heat is transferred from the furnace by radiation to a plurality of reactor tubes that conduct hydrocarbon flow. To attain high yield, the reaction must be quenched by rapidly lowering the hydrocarbon temperature after the reaction. The quench is usually achieved by conducting the hydrocarbon through a transfer line heat exchanger that boils water or by injecting cold oil into the hydrocarbon stream when fouling is a concern.

At the high temperature conditions present in the RFRs, OTA materials used in RFRs to date can suffer from poor strength, low stability, low activity, high pressure drop, high cost, environmental unsuitability, etc., especially after being subjected to repeated cycles of heating and cooling, oxidation and reduction, and so on. Other shortcomings of prior art include: 1) reactor fouling, which challenges operability and requires reactors to be taken offline; 2) maldistributions in flow or heat distribution, which accelerate fouling and compromise yield; 3) high $NO_x$ production due to high temperature combustion; 4) high furnace heat duty in part due to the reaction enthalpy and in part due to the need to heat up air and hydrocarbon to the reaction temperature; and 5) high yield of byproducts, that are expensive to separate—for example hydrogen byproduct must be compressed and cryogenically distilled from the ethylene product despite typically being used for furnace fuel.

Patent document WO 2021/025942, which is incorporated herein by reference in its entirety, discloses the use of a support comprising a mixed first metal-second metal oxide—in particular, a composite phase spinel of the formula $M^1_A M^2_B O_4$, wherein $M^1$ is the transition metal, $M^2$ is the second element, and A and B may range from 0.2 to 2.8 wherein the sum of A+B=3—to increase stability under thermal cycling conditions.

In general, composites may be prone to attrition due to different rates of thermal expansion of the different materials, which can lead to lost activity and reduced efficiency, as well as pressure drop increases and plugging. Often, techniques for strengthening materials for high temperature can result in inactivation or loss of efficiency of the material. It would be useful therefore to improve material integrity for use in high temperature reactors without substantial adverse impact on activity and efficiency.

BRIEF SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

This invention provides for a new catalyst with improved mechanical and chemical stability that is useful in a process to convert paraffin to olefin. The inventive catalyst comprises: Oxides of manganese, tungsten, and alkali (sodium, lithium, potassium) on a support comprising oxides of magnesium and aluminum.

In one aspect, the invention provides an active material, comprising:

an active phase comprising an oxide of a first element selected from transition metal elements, wherein the transition metal oxide is reversibly oxidizable and/or reducible between oxidized and reduced states, wherein the transition metal oxide is present in the oxidized state, the reduced state, or a combination thereof; and a support phase comprising an mixed metal oxide comprising a first metal selected from IUPAC Group 2-14 elements and a second metal selected from IUPAC Group 2-14 elements.

In some embodiments of the active material according to the invention, wherein the mixed metal oxide of the support phase has the formula $M^1_{x1}O_{y1}/M^2_{x2}O_{y2}$), wherein:

$M^1$ is the first metal selected from IUPAC Group 2-14 elements, where x1 and y1 may range from 1 to 3 and are chosen to have a neutral charge balance, $M^2$ is the second metal selected from IUPAC Group 2-14 elements where x2 and y2 may range from 1 to 3 and are chosen to have a neutral charge balance.

In certain embodiments of the active material according to the invention, $M^1$ and $M^2$ are independently selected from the group consisting of Al, Si, Mg, Ca, Sr, Ba, Sc, Y, La, Ce, Ti, Zr, Hf and Mn. In still other embodiments, $M^1$ is Mg and $M^2$ is selected from the group consisting of Al, Si, Ca, Sr, Ba, Sc, Y, La, Ce, Ti, Zr, Hf, Mn and mixtures thereof.

In other embodiments of the active material according to the invention, the mixed metal oxide comprises a first ceramic material and a second ceramic material. In particular embodiments, the first ceramic material and a second ceramic material are independently selected from the group consisting of alumina ($Al_2O_3$), silica ($SiO_2$), magnesia (MgO), ceria ($CeO_2$), titania ($TiO_2$), zirconia ($ZrO_2$), cordierite ($2MgO \cdot 2Al_2O_3 \cdot 2SiO_2$), mullite ($3Al_2O_3 \cdot 2SiO_2$), aluminum titanate ($Al_2TiO_5$), magnesium aluminate ($MgAl_2O_4$), calcium-stabilized zirconia ($CaO-ZrO_2$), magnesium-stabilized zirconia ($MgO-ZrO_2$), yttria-stabilized zirconia ($Y_2O_3-ZrO_2$), yttria ($Y_2O_3$), barium zirconate ($BaZrO_3$), strontium zirconate ($SrZrO_3$), and combinations thereof. In still other particular embodiments, the first ceramic material is magnesia (MgO) and the second ceramic material is alumina ($Al_2O_3$).

In some embodiments of the active material according to the invention, the ratio of the first metal and the second metal in the support phase is from about 10:1 to about 3:1. In particular embodiments, the ratio of the first metal and the second metal in the support phase is from about 7:1 to about 3:1; or from about 5:1 to about 3:1.

In other embodiments of the active material according to the invention, the transition metal oxide of the active phase comprises manganese.

In still other embodiments of the active material according to the invention, the oxidized state of the transition metal oxide comprises a spinel structure.

In yet other embodiments of the active material according to the invention, wherein the active phase further comprises a promoter that suppresses carbon oxidation in a redox reaction, preferably wherein the promoter is selected from tungsten, sodium, cerium, and combinations thereof, more preferably wherein the promoter comprises sodium tungstate. In certain embodiments, the promoter in the active phase comprises from 5 to 20 weight percent, based on the total weight of the active phase. In other embodiments, the promoter in the active phase comprises from 7 to 12 weight percent, based on the total weight of the active phase.

In some embodiments of the active material according to the invention, the active phase is doped with up to 20 percent by weight of the active phase of the second element, preferably wherein the second element comprises aluminum.

In other embodiments of the active material according to the invention, the active phase further comprises a selectivity modifier.

In some embodiments of the active material according to the invention, the active phase comprises from 1 to 20 percent by weight, based on the total weight of the active material. In particular embnodiments, the active phase comprises from 4 to 15 percent by weight, based on the total weight of the active material. In certain embodiments, the active phase comprises from 5 to 10 percent by weight, based on the total weight of the active material.

In some embodiments of the active material according to the invention, the oxidized state of the transition metal oxide comprises a spinel structure of the formula $M^1_3O_4$, wherein $M^1$ is a transition metal. In particular embodiments, $M^1$ is manganese.

In another aspect, the invention provides a reactor comprising the active material according to the invention disposed in a chemical looping reactor enclosure.

In another aspect, the invention provides a method for making the active material according to the, comprising the steps of:
  providing a substrate comprising the support phase; and
  coating the substrate with the active phase.

In certain embodiments, the method for making the active material further comprises doping the active phase, preferably manganese oxide, with a promoter, preferably sodium tungstate. In certain other embodiments, the method for making the active material further comprises doping the active phase, preferably manganese oxide, with the second element, preferably aluminum.

In another aspect, the invention provides a regenerative reaction process, comprising the sequential steps of:
  (a) disposing the active material according to the invention into a reactor member;
  (b) for a first period of time, contacting the oxidized state of the active phase of the active material in the reactor member with an oxidizable reactant at pressure, temperature, and flow rate conditions to reduce the active phase to the reduced state and form a reaction product;
  (c) for a second period of time, contacting the reduced state of the active phase of the active material in the reactor member with an oxidant to regenerate the active phase to the oxidized state for reduction in step (b); and
  (d) sequentially repeating steps (b) and (c) in the same reactor one or more times.

The catalyst enables a chemical looping process that comprises two steps. In a first step, paraffin converts to olefin and hydrogen by thermal pyrolysis or catalytic dehydrogenation. In a second step, the resulting hydrogen is selectively oxidized by oxygen in the catalyst of the invention. The oxygen-depleted catalyst is then removed from contact with the hydrocarbon and reoxidized by contacting with air. The process works particularly well with ethane conversion to ethylene, but may also be used with a feed of propane, butane, or naphtha and potentially even methane to make other olefins such as propylene or butylene. The process can be carried out in a circulating fluid bed reactor or a cyclic fixed bed reactor, such as a reverse flow reactor. The resulting process attains numerous efficiencies compared to steam cracking—for example, up to 33% lower energy use, 90% lower $CO_2$ emissions, and 15% lower capital expenditure.

DETAILED DESCRIPTION

Figure 1A:
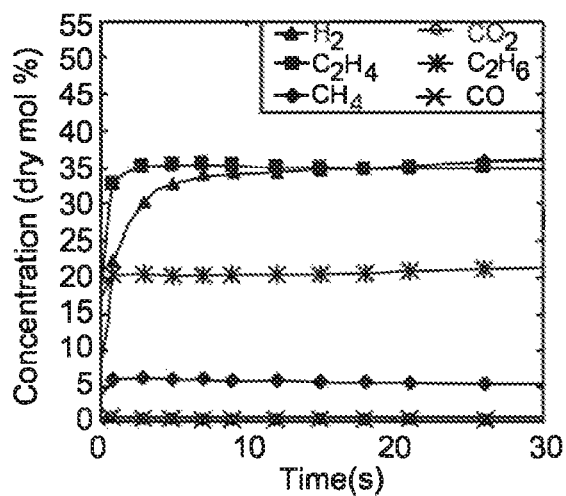
FIG. 1A is a graph showing the transient gaseous product composition from ethane feed gas at 850° C., 0.4 s residence time, 16 g/h WHSV, over 1.6 g of $Na_2WO_4$-promoted $Mn_2O_3$ supported on $\alpha$-$Al_2O_3$ (Example 1).

Throughout the entire specification, including the claims, the following terms shall have the indicated meanings. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of this disclosure described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the detailed description and the claims herein are modified by "about" or "approximately" the indicated value, and take into account experimental error and variations that would be expected by a person having ordinary skill in the art.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

The term "active" refers to substance having an element or compound that participates as a reactant in a chemical reaction and may optionally have catalytic characteristics.

The term "alkane" means substantially saturated compounds containing hydrogen and carbon only, e.g., those containing ≤1% (molar basis) of unsaturated carbon atoms. The term alkane encompasses $C_2$ to $C_6$ linear, iso, and cyclo alkanes.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "cycle time" means the time from a first interval to the next first interval, including (i) intervening second, third, and/or fourth intervals and (ii) any dead-time between any pair of intervals.

The term "flow-through reactor" refers to a reactor design in which one or more reagents enter a reactor, typically an elongated channel or stirred vessel, at an inlet, flow through the reactor, and then a product mixture (including any unreacted reagents) is continuously or semi-continuously collected at an outlet. Flow-through reactors include continuous reactors, as well as semi-continuous reactors in which one phase flows continuously through a vessel containing a batch of another phase, e.g., fixed-bed reactors where a fluid phase passes through a solid phase of catalyst, reactant, active material, etc.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of oxidative coupling, oxydehydrogenation and dehydrocyclization. Similarly, a "quench zone" or "quenching zone" is a location within the reactor for transferring heat from products of the catalytic hydrocarbon conversion, such as $C_{2+}$ olefin.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "oxidant" means any oxygen-bearing material which, under the conditions in the reaction zone, yields oxygen for transfer to the oxygen storage material, for storage with and subsequent release from the oxygen storage material to the oxidative coupling and/or oxydehydrogenation. While not wishing to be limited to theory, molecular oxygen atoms may be provided as a reactive gas in a gaseous zone and/or atomic oxygen may be provided from a catalyst surface as, for instance, reacted, sorbed forms.

The terms "oxidized state" and "reduced state" refer to relative states of oxidation and reduction with respect to a reference state. For example, in compositions of the formulae $Mn^{2+}_{A1}Mn^{3+}_{B1}O_x$ and $Mn^{2+}_{A2}Mn^{3+}_{B2}O_y$, where x<y, A1>A2, and B1<B2, $Mn^{2+}_{A1}Mn^{3+}_{A1}Mn^{3+}_{B1}O_x$ is the reduced state compound and $Mn^{2+}_{A2}Mn^{3+}_{B2}O_y$ is the oxidized state compound.

The term "oxydehydrogenation" means oxygen-assisted dehydrogenation of an alkane, particularly a $C_{2+}$ alkane, to produce an equivalent alkene and water.

The term "reaction stage" or "reactor stage" means at least one flow-through reactor, optionally including means for conducting one or more feeds thereto and/or one or more products away therefrom.

The term "residence time" means the average time duration for non-reacting (non-converting by oxidative coupling) molecules (such as He, $N_2$, Ar) having a molecular weight in the range of 4 to 40 to traverse the reactor or a defined zone within the reactor, such as a reaction zone of a oxidative coupling reactor.

The term "spinel" refers to the cubic crystalline structure of the spinel class of minerals typified by the mineral spinel, $MgAl_2O_4$, or a material having such a structure. A spinel has the general formula $AB_2X_4$, where X is an anion such as chalcogen, e.g., oxygen or sulfur, arranged in a cubic close-packed lattice, and A and B are cations, which may be different or the same, occupying some or all of the octahedral and tetrahedral sites in the lattice, also including the so-called inverse spinels where the B cations may occupy some or all of the typical A cation sites and vice versa. Although the charges of A and B in the prototypical spinel structure are +2 and +3, respectively, i.e., $A^{2+}B^{3+}_2X^{2-}_4$, other combinations incorporating divalent, trivalent, or tetravalent cations, including manganese, aluminum, magnesium, zinc, iron, chromium, titanium, silicon, and so on, are also possible.

The term "unsaturated" means a $C_n$ hydrocarbon containing at least one carbon atom directly bound to another carbon atom by a double or triple bond.

This disclosure provides an active material comprising an active phase and a support phase.

To address the issues discussed above in the production of olefins, a chemical looping system is used in which a metal oxide is contacted with the hydrocarbon stream in the reactor at 750-900° C. and oxygen in a metal oxide selectively oxidizes hydrogen in the product to steam. When oxygen is depleted from the metal oxide, the spent metal oxide is removed from the hydrocarbon stream and contacted with air to replenish oxygen and remove foulants. Ethylene is more easily separated from steam than hydrogen, which results in lower separation cost via reduced compression and refrigeration. The heat distribution is uniform because the heat output is proportional to the location of the metal oxide, which can easily by distributed evenly in a reactor. Finally, $NO_x$ production is lower because the maximum gas temperature is lower in the chemical looping system than a fired furnace.

Suitable reactors for chemical looping are circulating fluid beds reactors (CFBR) or cyclic fixed bed reactors, such as reverse flow reactors (RFR). The ideal reactor depends on the heat balance of the process. A CFBR is cooled by injecting cold feed gas, and is therefore suitable for processes with high $H_2$ conversion or high $CO_x$ yield. High $H_2$ conversion is desirable because it leads to the lowest cost of ethylene recovery. But, high $H_2$ conversion is associated with high $CO_x$ yield, which is very undesirable. Therefore, it is beneficial to operate at moderate $H_2$ conversion (e.g. 50-60%) to minimize $CO_x$. This requires a reactor with better heat integration than a CFBR because less heat is released at moderate $H_2$ conversion. Better heat integration is more difficult to provide in a CFBR because of limitations on feed preheating without initiating unselective pyrolysis in the feed heat exchangers. A RFR is just such a reactor with better heat integration and fast heat transfer. Therefore, a RFR is heat balanced with lower $H_2$ conversion and more importantly, low $CO_x$ yield. In addition, a RFR allows longer residence time of the solid in the reactor, while maintaining a short gas phase residence time. As a result, the RFR has less severe requirements for oxygen diffusivity in the solid than a CFBR, allowing more flexibility with the material design. However, one key problem with a RFR is that it is more difficult to change the catalyst than a CFBR. Therefore, a RFR requires a catalyst with a very long lifetime, preferably one year or longer.

A key aspect to enable chemical looping is the material chosen for the metal oxide. In the prior art, a metal oxide comprising oxides of manganese ($MnO_x$, with x between 1 and 1.5), tungsten ($WO_3$), and alkali (e.g., sodium, $Na_2O$, lithium, $Li_2O$, or potassium, $K_2O$, etc.) is disclosed as a suitable material to store oxygen and selectively oxidize hydrogen in the product. $MnO_x$ is the component that stores oxygen. $WO_3$ inhibits $CO_x$ yield. And alkali promotes the Mn-W interaction. Several supports for this process are disclosed, most notably single-component oxides of silica ($SiO_2$) or magnesia (MgO). These supports are undesirable for various reasons. A $SiO_2$ support sinters too easily thereby deactivating $MnO_x$. MgO is difficult to form into pellets, due to its chalky nature. Alumina ($Al_2O_3$) is known as a sinter-resistant, pellet-forming support, but $Al_2O_3$ forms a strong interaction with $MnO_x$, leading to inactive $MnAl_2O_4$. Notably, this strong Al—Mn interaction occurs even in supports that comprise mixed oxides of Si—Al, such as kaolin. Also, supports comprising mixed oxides of Mg—Si (fluorite) or Mg—Si—Al (cordierite) are also unsuitable.

The invention provides a novel support for the active phase components. In any embodiment, the inventive support comprises a mixed metal oxide. The support phase of the active material is a mixed metal oxide ($M^1_{x1}O_{y1}$/$M^2_{x2}O_{y2}$), wherein $M^1$ and $M^2$ are independently selected from the group consisting of Al, Si, Mg, Ca, Sr, Ba, Sc, Y, La, Ce, Ti, Zr, Hf and Mn. In particular embodiments, $M^1$ is Mg and $M^2$ is selected from the group consisting of Al, Si, Ca, Sr, Ba, Sc, Y, La, Ce, Ti, Zr, Hf and Mn. In certain embodiments, $M^1$ is Mg and $M^2$ is selected from the group consisting of Al, Si, Ca, Sr, Ba, Sc, Y, La, Ce, Ti, Zr, Hf, Mn and mixtures thereof. As non-limiting illustrative examples, the support phase can be a mixture of two or more of silica ($SiO_2$), magnesia (MgO), ceria ($CeO_2$), titania ($TiO_2$), zirconia ($ZrO_2$), cordierite ($2MgO\ 2Al_2O_3\ 2Si_2$), mullite ($3Al_2O_3\ 2SiO_2$), aluminum titanate ($Al_2TiO_5$), magnesium aluminate ($MgAl_2O_4$), calcium-stabilized zirconia (CaO—$ZrO_2$), magnesium-stabilized zirconia (MgO—$ZrO_2$), yttria-stabilized zirconia ($Y_2O_3$—$ZrO_2$), yttria ($Y_2O_3$), barium zirconate ($BaZrO_3$), and strontium zirconate ($SrZrO_3$). A mixture of magnesia (MgO) and aluminum oxide ($Al_2O_3$, a.k.a. alumina) is a preferred support phase, and is referred to herein in the following discussion by way of example for the purposes of simplicity and clarity. $Al_2O_3$ can be in various crystallographic forms, including but not limited to, alpha-$Al_2O_3$, theta-$Al_2O_3$, and gamma-$Al_2O_3$.

In any embodiment, the content of each metal oxide is generally not limited. However, the inventors have found that having a larger proportion of magnesia than alumina is generally more effective at achieving the effects of the invention. In certain embodiments, the ratio of magnesia to alumina is from about 10:1 to about 3:1. In other embodiments, the ratio of magnesia to alumina is from about 7:1 to about 3:1. In still other embodiments, the ratio of magnesia to alumina is from about 5:1 to about 3:1

The mixed metal oxide may be co-mingled by standard methods, such as by ball-milling or mixing in a slurry phase. The support can be formed by sintering the mixed metal oxides into a desired shape.

In one aspect, the mixed metal oxide can be prepared by preparing a mixture of metal nitrates followed by reaction with a base solution in water. In certain embodiments, the base solution comprises a mixture of sodium carbonate and sodium hydroxide. In certain embodiments the base solution comprises only sodium hydroxide. In certain embodiments, a mixed base solution and a single based solution can be used, simultaneously or in sequence. The reaction of the metal nitrates with the base solution(s) is preferably performed at a constant pH, e.g., pH 10.

The support phase can be any shape. Some non-limiting examples include honeycomb monoliths, foams, pellets, and beads in spherical, ellipsoidal, and polyhedral shapes. In a reverse flow reactor, a honeycomb monolith is a preferred shape of the support phase. In a fluidized bed reactor, a solid granular material is shaped as tiny spherical beads that can be suspended at high enough velocities and cause them to behave as though it were a fluid.

In any embodiment, the active phase can comprise an oxide of a first element selected from transition metal elements. The transition metal oxide is reversibly oxidizable and/or reducible between oxidized and reduced states. The transition metal oxide may be present in the oxidized state, the reduced state, or a combination thereof. The support phase generally comprises an oxide of a second element selected from IUPAC Group 2-14 elements.

The oxidation state of the transition metal oxide is generally determined by temperature and oxygen partial pressure of the process conditions, and the transition metal oxide is present in the oxidized state, the reduced state, or a combination thereof. Any suitable transition metal oxide that is stable at high temperatures, economical, and environmentally benign, may be used in the active phase. For the purposes of clarity and convenience, the following discussion addresses manganese as a preferred example of the active phase transition metal.

In the oxidized state, manganese oxide can be any of a variety of manganese oxides including manganese(II) oxide (MnO), manganese(II, III) oxide ($Mn_3O_4$), manganese(III) oxide ($Mn_2O_3$), manganese(IV) oxide ($MnO_2$, a.k.a manganese dioxide), manganese(VI) oxide ($MnO_3$), and manganese(VII) oxide ($Mn_2O_7$). In the reduced state, the manganese can be metallic (Mn(0)), or any lesser oxidized manganese oxide than the oxidized state. By way of example, the oxidized state of the manganese can be $Mn_2O_3$, and the reduced state can be MnO. The oxidized state of the transition metal oxide preferably comprises a spinel structure.

In any embodiment, the active phase can further comprise doping with the second element of the support phase. As a non-limiting example, aluminum-doped manganese oxide (1:10 Al:Mn) can be prepared by dissolving an appropriate quantity of aluminum isopropoxide into water, heating the mixture at 90° C. for 1 h while stirring, combining with an aqueous solution of manganese acetate, concentrating the resulting mixture at 90° C., and then calcining the resulting gel at 900° C. for 2 h and cooling to ambient temperature. Optionally, sodium and tungsten can be added by dissolving a sodium source (e.g., sodium hydroxide), a tungsten source (e.g., tungstic acid), and optionally, an amine (e.g., triethanolamine) in water, adding the resulting solution to manganese oxide, and calcining at 900° C. for 2 h.

The $MnO_x$ phase can be any of those listed above (e.g., $Mn_2O_3$, $Mn_3O_4$, MnO). The lattice constant of the $MnO_x$ phase may be shifted from pure $MnO_x$, which indicates incorporation of $Al_2O_3$ into the $MnO_x$ phase. For example, the $MnO_x$ phase may be $Mn_2O_3$ structure (space group #206) with a lattice constant of 9.33 Å, which compares to a lattice constant of 9.41 Å for pure $Mn_2O_3$. Optionally, the aluminum-doped manganese oxide phase may be mixed with additional non-doped manganese material. In this case, the aluminum-doped manganese oxide phase may comprise the material with the diffraction pattern described above. In another embodiment, the mixed aluminum-manganese phase may comprise the spinel structure, $(Mn,Al)_3O_4$. These phases may be co-mingled by standard methods, such as by ball-milling or mixing in a slurry phase. The manganese oxide active phase and/or composite phase can be applied on the support phase by a wash coating method. The manganese oxide active phase can be a fine oxide powder or precursors of the oxide phase. As non-limiting illustrative examples, the precursors can be carbonates, nitrates, sulfates, chlorides, alkoxides of metallic manganese. Fine oxide powder or precursors of the active oxide phase can be mixed to achieve a desired mass ratio of the active phase and the support phase.

In the manganese oxide-based active materials, the active phase is preferably present in the range of 1 to 25 wt % based on the total weight of the active material, including the active phase, support phase, and composite phase. Preferably, the active phase is in the range of 3 to 15 wt. %. More preferably, the active phase is in the range of 5 to 10 wt. %.

In any embodiment of this disclosure, the active phase can include an alkali component or a promoter, which can effectively suppress the undesired $CO_x$ formation during the redox process in an oxidative dehydrogenation (ODH) reaction. A preferred ODH promoter is sodium tungstate ($Na_2WO_4$) or lithium tungstate ($Li_2WO_4$) which are mentioned in the following discussion for the purposes of illustrative simplicity and clarity. As non-limiting illustrative examples, the precursors of sodium tungstate or lithium tungstate can be carbonates, nitrates, sulfates, chlorides, alkoxides of metals comprising sodium and tungsten. The precursors of sodium tungstate or lithium tungstate can be mixed to achieve a desired mass ratio of the active phase. In the manganese oxide based active phase, the promoter is preferably in the range of 5 to 20 wt %, and more preferably in the range of 7 to 12 wt %, based on the total weight of the manganese oxide active phase.

In any embodiment of this disclosure, the active phase may further comprise a selectivity additive, e.g., cerium, to give preferential selectivity for hydrogen oxidation in an ODH system. As a non-limiting example, cerium nitrate in water is applied to $Mn_3O_4$ powder support for incipient wetness impregnation, and dried. Subsequently, a mixture of ammonium metatungstate and sodium tungstate in water can applied to the treated $Mn_3O_4$ powder for incipient wetness impregnation and again dried. The material (1:1 W:Ce by mole) can then be calcined at 1100° C.

One aspect in this disclosure is to improve adhesion of the manganese oxide active phase on the support phase by a wash coating method. Due to the thermal expansion mismatch between manganese oxide and the mixed metal support phase, the wash coated manganese oxide tends to detach from the support phase. This issue can be overcome by forming an intermediate layer of the composite phase through a proper pretreatment method.

The active material can be used in any reactor where an oxygen transfer agent is needed, preferably in an oxidative dehydrogenation (ODH) reactor. For example, the active material can be used in an ODH chemical looping reactor such as an RFR where the active material replaces the conventional fuel-oxidant combustion system. In this case, the active materials can be fabricated in a shape of a honeycomb monolith and placed in the middle of the RFR. Using the active material in an RFR in this format: a) avoids or significantly reduces the need to provide separate fuel for the regeneration step, eliminating the challenges with the combustion system in an RFR, b) selectively transfers oxygen to the endothermic reaction, which could potentially enable new chemistries or drive the reaction equilibrium forward in other cases, and c) simplifies reactor operation and downstream product handling.

Figure 9:
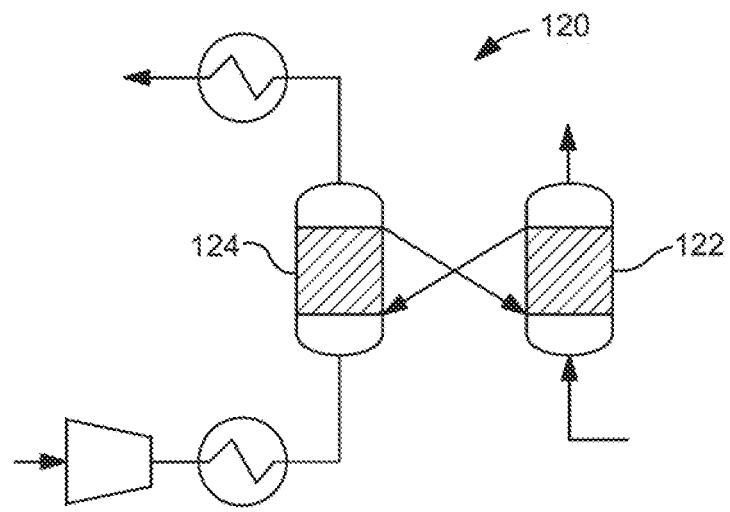
FIG. 9 is a simplified schematic diagram of a fluidized bed reactor according to embodiments of this disclosure.

Similarly, the same chemical looping oxidative dehydrogenation process can be realized in a fluidized bed reactor process 120 as shown in FIG. 9, which shows the schematic of a fluidized bed reactor system 120 for converting ethane to ethylene with reactor 122 and regeneration of the active material with air in regenerator 124. In this case the active materials can be fabricated in a shape of a particle that enables circulation between the reactor 122 and the regenerator 124. In this two-step process, the active material donates oxygen from its lattice to convert ethane to ethylene and water in the reactor 122. After the active material is reduced, it is transferred back to the regenerator 124 to complete the redox cycle. This fluidized bed process scheme eliminates drawbacks of conventional ODH because an expensive air separation unit is no longer required, and the overall process is safer since ethane is not mixed with oxygen. This scheme also reduces energy consumption and $CO_2$ emissions in comparison with steam crackers due to selective oxidation of hydrogen that provides energy needed for the ethane dehydrogenation. Moreover, higher single pass yields of ethylene and in-situ hydrogen oxidation reduces the load for the downstream separation and purification steps. With proper design of the active materials to avoid over-oxidation of ethane or ethylene, the use of lattice oxygen in the active materials can also lead to higher ethylene selectively. The presently disclosed process can incorporate reactors, systems, and reaction processes for contacting hydrocarbon reactant in the presence of oxygen stored and released from the active material. The active material can often be one having thermal mass, or alternatively or in addition, can be located proximate to, on, or within a thermal mass located in at least one region of the reactor. The heat in the reactor and the presence of the active material result in the formation of olefin products along with steam, carbon monoxide, and/or carbon dioxide. While not wishing to be bound by any theory or model, it is believed that a part of the conversion process is a result of thermal or catalytic dehydrogenation of the hydrocarbons to olefins and hydrogen, followed by a subsequent step in which hydrogen or hydrocarbons react with oxygen from the active material to form water, carbon monoxide, and carbon dioxide.

One suitable reaction process incorporating the active material according to the present disclosure is exemplified the oxydehydrogenation (ODH) reaction according to the equation:

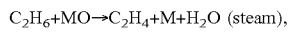

$C_2H_6 + MO \rightarrow C_2H_4 + M + H_2O$ (steam), wherein MO is a metal oxide that can comprise one or more transition metal oxides, such as of manganese or tin, and which can further comprise one or more of magnesium, calcium, strontium, aluminum, cobalt, zirconium, yttrium, cerium, lanthanum, silicon, titanium, sodium, tungsten, or so on.

In any embodiment the exothermic regeneration of the active material during the regeneration step can provide the heat necessary to conduct the subsequent endothermic reaction in the reaction step, thereby eliminating fuel-air based combustion systems and the accompanying generation of carbon oxides and coke, and simplifying reactor design significantly. The disclosed method has advantages over other reactor systems (e.g., circulating fluid beds) that could employ the described active material, due to better thermal management and less agitation of the active material.

Oxygen storage and release for carrying out the hydrocarbon conversion is achieved by regenerating the active material. In certain aspects, a thermal mass is utilized which comprises, consists essentially of, or consists of active material. Oxygen is transferred from an oxidant to the active material for storage within the active material. Oxygen is typically transferred and stored as the oxidant is passed through the thermal mass region of the reactor. Oxygen can be transferred from the oxidant to the active material for storage with the active material in any form, e.g., as oxygen atoms, oxygen ions, or as a component of an oxygen-containing molecule (e.g., an oxygen precursor). Stored oxygen released from the active material for reacting with the hydrocarbon reactant to produce the first reaction mixture can be in any form, e.g., as oxygen atoms, oxygen ions, or as a component of an oxygen-containing molecule (e.g., an oxygen precursor).

Storage of the oxygen causes the thermal mass to be heated. For example, storage of the oxygen can be accompanied by exothermic reaction with the thermal mass. Thus, the oxidant itself can be considered a heating fluid for heating the flow-through reactor. The regeneration step often proceeds according to the equation:

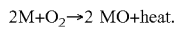

$2M + O_2 \rightarrow 2\ MO + \text{heat}$.

Presented herein is a process for converting a $C_1$ to $C_6$ alkane to a $C_2$ to $C_6$ olefin, comprising passing an oxygen-containing gas in a first direction through a reverse flow reactor (RFR); contacting the oxygen-containing gas with an active material comprising a metal oxide to heat the reactor; terminating the oxygen-containing gas flow; optionally purging the oxygen-containing gas from the reactor with steam, inert gas, or vacuum purge; passing a $C_1$ to $C_6$ alkane stream through the reactor in a second direction and past the active material; reacting oxygen from the oxygen transfer agent with the $C_1$ to $C_6$ alkane under conditions sufficient to form $C_2$ to $C_6$ olefin and steam; optionally purging the $C_1$ to $C_6$ alkane and olefin from the reactor with steam or inert gas; and withdrawing an effluent comprising the $C_2$ to $C_6$ olefin from the reactor.

Figure 10:
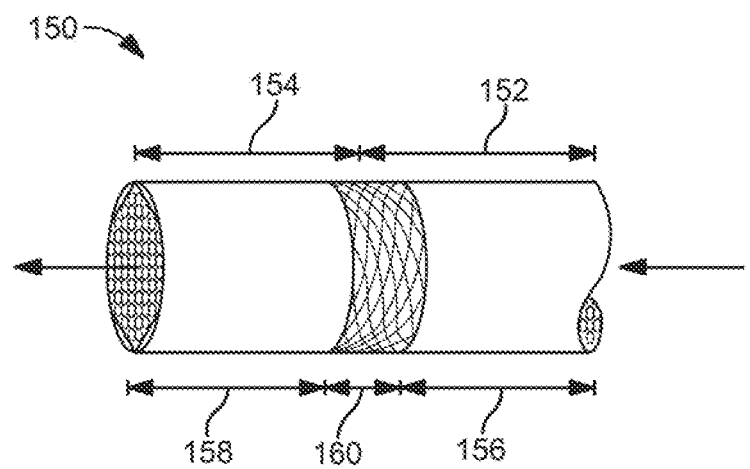
FIG. 10 is a simplified schematic diagram of a flow-through reactor according to embodiments of this disclosure.

FIG. 10 illustrates a flow-through reactor, for example a reverse-flow reactor 150 having a first region 152 and a second region 154, with the first and second regions 152, 154 comprising thermal mass. Valves, for example poppet valves or another suitable type of valve, are used to regulate flows of all gases entering and exiting the reactor. The process described herein, however, is not limited to being conducted in reverse flow reactors having two regions, and the FIG. 10 description is not intended to foreclose other configurations of thermal mass. For example, the thermal mass material may be coupled together as a continuous mass in a single region or more than one region or separate thermal masses may be coupled together, forming more than one region. As another example, the thermal mass can be a continuous mass of a ceramic material having an oxygen-storage functionality.

The terms first and second thermal mass segments are used for convenience in FIG. 10 to particularly describe the heating and cooling of the regions of the thermal mass as the oxygen transfer reaction progresses through the flow of the feeds and conversion products through the reactor. The reaction being carried out results in sorption and release of heat in a manner that is effective in the continuous conversion of alkanes in the hydrocarbon reactant feed to produce a reaction mixture comprising $C_2$ to $C_6$ olefin compositions.

The reactor in FIG. 10 includes a continuous thermal mass, which is represented as a first thermal mass segment 156 and a second thermal mass segment 158, with the thermal mass including a reaction zone 160. The reaction zone 162 comprises at least one active material, which can be further incorporated on or in either or both of the thermal mass segments 156, 158. For example, all of the active material can be incorporated in or on either thermal mass segment 156 or thermal mass segment 158 or a portion of the active material can be incorporated in or on both thermal mass segment 156 and thermal mass segment 158. Advantageously, the active material is incorporated primarily in reaction zone 160.

Figure 11:
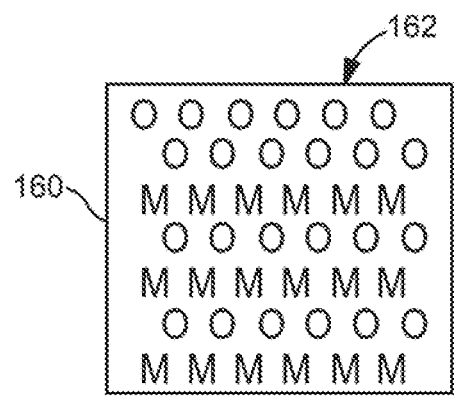
FIG. 11 is a simplified schematic diagram of an active material in an oxidized state according to embodiments of this disclosure.
Figure 12:
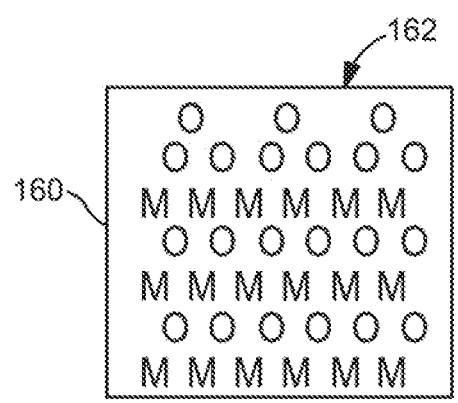
FIG. 12 is a simplified schematic diagram of the active material of the invention in a reduced state according to embodiments of this disclosure.

FIGS. 11 and 12 are a characterization of a cross-sectional enlargement of the reaction zone 160 in an oxidized state following regeneration as seen in FIG. 11, or in a reduced state following contribution of oxygen atoms to an ODH reaction as seen in FIG. 12. "M" in FIGS. 11-12 refers to a metal center, representative of at least one active material.

"O" in FIGS. 11-12 refers to an oxidant such as oxygen, which has been stored in the reaction zone 160 in FIG. 11 from a regeneration step in which heating fluid comprising an oxidant is flowed through the reactor. Conversely, the oxidant "O" is at least partially depleted from the reaction zone 160 in FIG. 12 following a reaction step in which reactant feed comprising $C_2$ to $C_6$ alkanes is flowed through the reactor and converted to the corresponding olefin and the hydrogen produced converted by reaction with the oxygen from the active phase to water.

As seen in FIG. 11, oxygen from the oxidant can be stored in a portion of the thermal mass of the reaction zone containing active material "M". As the oxidant is flowed through the reactor, at least a portion of the oxidant (i.e., oxygen) is stored with the active material. The oxygen can migrate from the surface 162 of the thermal mass toward a more central region of the thermal mass, becoming more deeply embedded in the thermal mass. As flow of oxidant continues, the storage of oxygen can reach a maximum or saturation-type level.

As the hydrocarbon reactant (e.g., ethane) is flowed through the reactor, the stored oxygen is released as shown in FIG. 12, and oxidatively dehydrogenates the alkane in the hydrocarbon reactant to produce a reaction mixture comprising a $C_{2+}$ olefin composition, with minimal amounts of carbon oxides, hydrogen and coke formed.

Operating pressures may include a pressure of at least atmospheric pressure (zero pressure, gauge), such as ≥4 pounds per square inch gauge (psig) (28 kilopascals gauge (kPag)), or ≥10 psig (69 kPag), or ≥36 psig (248 kPag), or ≥44 psig (303 kPag), or ≥103 psig (709 kPag), but may be ≤300 psig (2064 kPag), or ≤100 psig (689 kPag), or ≤30 psig (206 kPag).

Residence times in the reactor (including any recuperative preheat and quench) may be ≤10 seconds and even ≤5 seconds, or in the range of 0.005 seconds to 5 seconds, 0.01 seconds to 3 seconds, 0.02 seconds to 1.5 seconds, or 0.05 to 1 seconds. For a reverse-flow reactor, the process may operate at cycle times ≤0.5 second, such as in the range of 1 second to 240 seconds, in the range of 5 seconds to 120 seconds, in the range of 10 seconds to 90 seconds, or in the range of 20 seconds to 60 seconds.

Also, as may be appreciated, these different pressures and residence times may be utilized together to form different combinations depending on the specific configuration of equipment.

Figure 8:
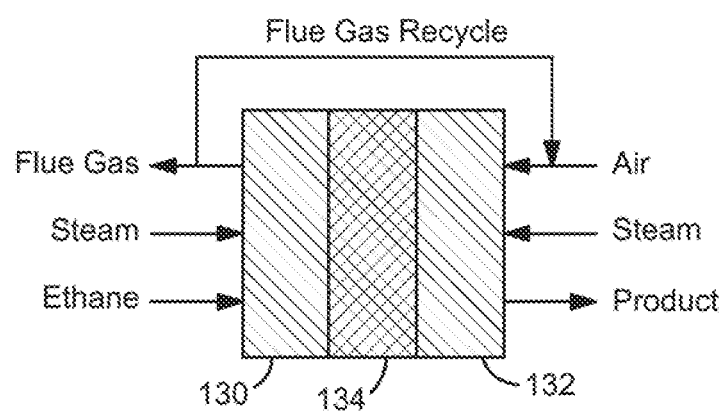
FIG. 8 is a simplified schematic diagram of an RFR according to embodiments of this disclosure.

FIG. 8 is a schematic view of one advantageous configuration for the RFR used to conduct the presently disclosed process, which comprises: (1) In-flows of $C_2$-$C_6$ hydrocarbon, air, flue gas recycle, and steam; (2) Out-flows of flue gas and reaction product; (3) a recuperative section 130 for heat exchange (preheat) between flue gas and ethane; (4) a recuperative section 132 for heat exchange (quench) between air and reaction product; and (5) a section 134 comprising the active material. The flows may be regulated by valves.

The reactor operation comprises alternating flow of streams comprising air and hydrocarbon. In some embodiments, steam or inert gas is flowed to purge air or hydrocarbon from the reactor between switches from regeneration flow and product formation flow. In other embodiments, the purge is accomplished by applying vacuum or a combination of vacuum, steam, or inert gas. In yet other embodiments, no purge is applied. The temperature of the effluents is controlled by the level of flue gas recycle and the size of the heat exchange sections. The product yield is controlled by the intrinsic active material properties, the loading of active material in the reactor, and the duration for which hydrocarbon is flowed to the reactor.

When used in an RFR, the active materials disclosed herein enable very high yields of ethylene from hydrocarbon feeds, such as those comprising ethane, propane, butane, or naphtha. The active material releases oxygen when contacted with hydrocarbons during a reaction step, leading to the formation of primarily ethylene, steam, and other olefins (endothermic reactions). The yields of carbon oxides, hydrogen, methane, and other alkanes are suppressed.

The regenerated active material comprises the oxidized state of the active material. The active material can be packed in the reactor in the form of pellets, washcoated ceramic monoliths, such as honeycomb monoliths, which have at least one channel for establishing the specified flows of oxidant and hydrocarbon reactant. The active material may also be extruded in the form of such a monolith.

A relative flow of oxygen-containing gas and $C_2$-$C_6$ alkane are sufficient to achieve effluent temperatures below 400° C., or above 550° C. For example, the weight ratio of the flow rates of oxidizer gases (e.g., air, flue gas recycle, and steam) to ethane can be between 2.4 to 3.0. Low-temperature effluent is advantageous because it requires less capital to recover heat as steam. A heat exchanger can be used to recover heat from the reactor effluents, by boiling water to make steam. When the effluent is recovered at a higher temperature, it is possible to generate high pressure steam by flowing it though a boiler. The high pressure steam can be used to supply the purge steam to the reactor and for other purposes, such as generating work in a turbine expander.

The active materials disclosed herein are not limited to use in an RFR. The reactor can be a reverse flow reactor, a circulating fluid bed reactor, or even a co-flow cyclic reactor. The process for converting a $C_1$ to $C_6$ alkane to a $C_2$ to $C_6$ olefin can comprise passing an oxygen-containing gas through a reactor; contacting the oxygen-containing gas with an oxygen transfer agent such as those described above to sorb the oxygen and heat the reactor; terminating the oxygen-containing gas flow; optionally purging the oxygen-containing gas from the reactor with steam, inert gas, or vacuum; passing a $C_1$ to $C_6$ alkane stream through the reactor past the oxygen transfer agent; desorbing oxygen from the oxygen transfer agent; reacting the desorbed oxygen with the $C_1$ to $C_6$ alkane under conditions sufficient to form $C_2$ to $C_6$ olefin and steam; and optionally purging the $C_1$ to $C_6$ alkane and olefin from the reactor with steam, inert gas, or vacuum.

EXAMPLES

The invention is demonstrated by these illustrative examples.

These examples demonstrate the concept can be advantageously utilized to improve ethane pyrolysis yields, reduce fuel demand, eliminate the fuel-oxidant based combustion system, and/or simplify the RFR design.

Example 1. (Comparative)

Synthesis of $Na_2WO_4/MnO_x$ Supported on $\alpha$-$Al_2O_3$ (100 wt. % $Al_2O_3$)

5.0 g of UniSpheres catalyst carrier ($\alpha$-$Al_2O_3$, 3 mm diameter spheres) provided by Saint-Gobain (catalog number SA 52124) were pre-calcined at 750° C. for 8 h (5° C./min ramp rate) under static air. In a vial, manganese(II) acetate tetrahydrate (6.6536 g) was dissolved in a mixture of 14 mL DI water and 1.5 mL glacial acetic acid. This solution was subsequently applied onto the support in successive coats by incipient wetness impregnation followed by calcination in between applications at 450° C. for 2 h (10° C./min ramp rate). After the addition of the manganese(II) acetate solution was completed, the material was calcined at 900° C. for 4 h (5° C./min ramp rate) under static air. Sodium tungstate dihydrate (0.1003 g) was dissolved in 0.25 g of DI water in a vial. To this solution, 0.25 g of triethanolamine was added. To the resulting solution, 2.5 g of the calcined solid was added. The vial was capped, and the contents of the vial were shaken to incorporate. The material was dried in a drying oven at 110° C. for 18 h, transferred to a crucible, and then calcined at 900° C. for 4 h (5° C./min ramp rate) under static air.

Example 2. (Comparative)

Synthesis of $Na_2WO_4/MnO_x$ Supported on $\theta$-$Al_2O_3$ (100 wt. % $Al_2O_3$)

The synthesis followed the same procedure as described above, except $\theta$-$Al_2O_3$ was used in the place of $\alpha$-$Al_2O_3$.

Example 3. (Comparative)

Synthesis of $Na_2WO_4/MnO_x$ Supported on Kaolin ($Al_2Si_2O_5(OH)_4$, =40 wt. % $Al_2O_3$, 47 wt. % $SiO_2$, 13 wt. % $H_2O$)

Manganese(II) acetate tetrahydrate (4.14 g) was dissolved in a mixture of 8.4 g of DI water and 0.5 mL of glacial acetic acid in 20 mL scintillation vial. The solution was subsequently applied onto 4.0 g of kaolin (FG-5, Active Minerals) in successive coats by incipient wetness impregnation followed by calcination in between applications at 450° C. for 2 h (10° C./min ramp rate). After the addition of the manganese(II) acetate solution was completed, the material was calcined at 900° C. for 4 h (5° C./min ramp rate) under static air and then ground with use of a mortar and pestle. Sodium tungstate dihydrate (0.632 g) was dissolved in 0.5 g of DI water in a vial. To this solution, 0.5 g of triethanolamine was added, and the resulting solution was applied to 4.0 g of the calcined solid. The material was dried in a drying oven at 110° C. for 18 h, transferred to a crucible, and then calcined at 850° C. for 8 h (5° C./min ramp rate) under static air.

Example 4. (Comparative)

Synthesis of $Na_2WO_4/MnO_x$ Supported on $SiO_2$ (100 wt. % $SiO_2$)

The synthesis followed the same procedure as described above, except silica (Sigma-Aldrich, 55 m2/g) was used in the place of kaolin.

Example 5. (Comparative)

Synthesis of $Na_2WO_4/MnO_x$ Supported on $MgSiO_3$ (40 wt. % MgO, 60 wt. % $SiO_2$)

The synthesis followed the same procedure as described above, except magnesium silicate was used in the place of kaolin.

Example 6. (Comparative)

Synthesis of $Na_2WO_4/MnO_x$ Supported on Quartz (100 wt. % $SiO_2$)

The synthesis followed the same procedure as described above, except quartz was used in the place of kaolin.

Example 7. (Comparative)

Synthesis of $Na_2WO_4/MnO_x$ Supported on MgO (100 wt. % MgO)

The synthesis followed the same procedure as described above, except magnesia was used in the place of kaolin.

Example 8. (Comparative)

Synthesis of $Na_2WO_4/MnO_x$ Supported on Cordierite ($Mg_2Al_3Si_5O_{18}$=15 wt. % MgO, 29 wt. % $Al_2O_3$, 56 wt. % $SiO_2$)

The synthesis followed the same procedure as described above, except cordierite powder (99.9%, 1-5 μm, Reade Advanced Materials) was used in the place of kaolin.

Example 9. (Inventive)

Synthesis of $Na_2WO_4/MnO_x$ Supported on $MgAl_2O_4$ (28 wt. % MgO, 72 wt. % $Al_2O_3$)

The synthesis followed the same procedure as described above, except magnesium aluminate was used in the place of kaolin.

Example 10. (Inventive)

Synthesis of $Na_2WO_4/MnO_x$ Supported on 70% MgO-30% $Al_2O_3$ (Sasol, MG70)

The synthesis followed the same procedure as described above, except Pural MG70 (Sasol) was used in the place of kaolin.

Example 11. (Inventive)

Synthesis of $Na_2WO_4/MnO_x$ Supported on Magnesia—Alumina (5:1 Mg:Al, 80 wt. % MgO, 20 wt. % $Al_2O_3$)

Magnesium nitrate hexahydrate (107.05 g) and aluminum nitrate nonahydrate (31.267 g) were dissolved in DI water in a 250 mL volumetric flask. Sodium carbonate (13.243 g) was dissolved in 125 mL DI water and combined with 125 mL of a 2.0 M solution of sodium hydroxide in a beaker. To a 2 L beaker, 500 mL DI water and a PTFE stir bar were added and heated to 40° C. A pH meter was fixed in the beaker to monitor pH, and the mixed base solution was used to adjust the pH to 10. While stirring at 40° C., the nitrate salt solution and the mixed base solution were added slowly to the 2 L beaker while maintaining the pH at 10. After the mixed base solution was fully consumed, 2.0 M sodium hydroxide solution was used as the base. Once all of the nitrate salt solution was consumed, the beaker was topped with a watch glass and stirred for 4 h at 40° C. The temperature was then increased to 70° C. and allowed to stir for 40 h. The reaction mixture was allowed to cool to rt, and solids were collected by vacuum filtration and washed thoroughly with water. The solids were allowed to dry in a drying oven at 100° C. Manganese(II) acetate tetrahydrate (4.14 g) was dissolved in a mixture of 6.4 g of DI water and 0.5 mL of glacial acetic acid in 20 mL scintillation vial. The solution was subsequently applied onto 4.0 g of the dried solid in successive coats by incipient wetness impregnation followed by calcination in between applications at 450° C. for 2 h (10° C./min ramp rate). After the addition of the manganese(II) acetate solution was completed, the material was calcined at 900° C. for 8 h (5° C./min ramp rate) under static air. Sodium tungstate dihydrate (0.56 g) was dissolved in 0.5 g of DI water in a vial. To this solution, 0.5 g of triethanolamine was added, and the resulting solution was applied to the calcined solid. The material was dried in a drying oven at 110° C. for 18 h, transferred to a crucible, and then calcined at 850° C. for 8 h (5° C./min ramp rate) under static air.

Example 12. (Inventive)

Synthesis of $Na_2WO_4/MnO_x$ Supported on Magnesia—Alumina (70 wt. % MgO, 30 wt. % $Al_2O_3$, 3:1 Mg:Al)

Magnesium nitrate hexahydrate (96.34 g) and aluminum nitrate nonahydrate (46.89 g) were dissolved in DI water in a 250 mL volumetric flask. Sodium carbonate (13.243 g) was dissolved in 125 mL DI water and combined with 125 mL of a 2.0 M solution of sodium hydroxide in a beaker. To a 2 L beaker, 500 mL DI water and a PTFE stir bar were added and heated to 40° C. A pH meter was fixed in the beaker to monitor pH, and the mixed base solution was used to adjust the pH to 10. While stirring at 40° C., the nitrate salt solution and the mixed base solution were added slowly to the 2 L beaker while maintaining the pH at 10. After the mixed base solution was fully consumed, 2.0 M sodium hydroxide solution was used as the base. Once all of the nitrate salt solution was consumed, the beaker was topped with a watch glass and stirred for 4 h at 40° C. The temperature was then increased to 70° C. and allowed to stir for 40 h. The reaction mixture was allowed to cool to rt, and solids were collected by vacuum filtration and washed thoroughly with water. The solids were allowed to dry in a drying oven at 100° C. Manganese(II) acetate tetrahydrate (5.175 g) was dissolved in a mixture of 10.5 g of DI water and 0.5 mL of glacial acetic acid in 20 mL scintillation vial. The solution was subsequently applied onto 5.0 g of the dried solid in two successive coats by incipient wetness impregnation followed by calcination in between applications at 450° C. for 2 h (10° C./min ramp rate). After the addition of the manganese(II) acetate solution was completed, the material was calcined at 900° C. for 8 h (5° C./min ramp rate) under static air. Sodium tungstate dihydrate (0.632 g) was dissolved in 0.5 g of DI water in a vial. To this solution, 0.5 g of triethanolamine was added, and the resulting solution was applied to 4.0 g of the calcined solid. The material was dried in a drying oven at 110° C. for 18 h, transferred to a crucible, and then calcined at 850° C. for 8 h (5° C./min ramp rate) under static air.

Example 13. (Comparative)

Manganese(III) oxide was extruded with silica (Versal 300) to attain 1/16 inch quadrulobes with 25 wt. % manganese oxide. Sodium tungstate dihydrate (0.32 g) and ammonium metatungstate hydrate (0.28 g) were dissolved in 0.5 g of DI water in a vial. To this solution, 0.5 g of triethanolamine was added, and the resulting solution was applied to 4.0 gram of the manganese oxide extrudate. The material was dried in a drying oven at 110° C. for 18 h, transferred to a crucible, and then calcined at 850° C. for 8 h (5° C./min ramp rate) under static air.

Example 14—In Situ Powder X-Ray Diffraction Analysis

Chemical looping reactivity studies on various support compositions indicated that while pure alumina as a support led to inactive materials, the presence of excess magnesia in the support yields materials that demonstrate activity for the chemical looping conversion of ethane to ethylene. This example provides greater understanding of the functions and dispositions of the various components of the magnesium aluminate-based compositions during redox cycling using PXRD analysis. To ensure that the characterization reflected the nature of the materials under more realistic conditions, performed analyses of the magnesium aluminate-supported samples were performed in situ, at reaction temperature (850° C.) and under humidified reducing (4% $H_2$ in $N_2$) or oxidizing (air) gas environments. The resulting PXRD traces are shown in FIG. 13 for the three samples in which the Mg:Al ratio is greater than 1:2.

When the samples are heated to temperature (850° C.) in air, sodium in the form of sodium tungstate is no longer observable by PXRD as it was at room temperature. The melting point for sodium tungstate is only 698° C., so it is liquefied and crystallographically disordered at these conditions. Consequently, the PXRD traces for the samples of supported manganese oxide containing 3:1 Mg:Al with and without the addition of sodium tungstate are essentially indistinguishable.

Figure 13:
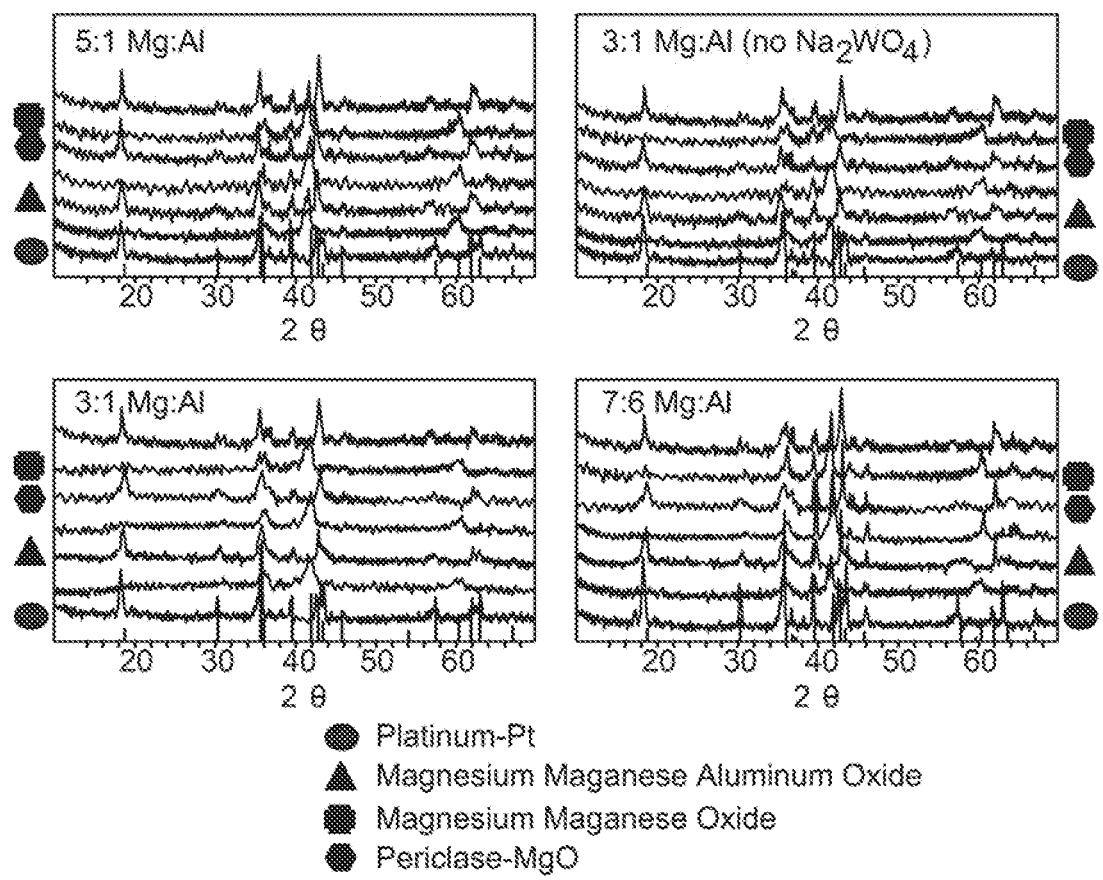
FIG. 13 shows powder X-ray diffractograms of magnesium aluminate-supported, sodium tungstate-promoted manganese oxides under humidified reducing (4% H$_2$ in N$_2$) or oxidizing (air) gas environments. Initial samples at 1123 K under air (black), after first reduction (light blue), after first re-oxidation (orange), after first re-reduction (yellow), after second re-oxidation (green), after second re-reduction (purple), and after third re-oxidation (red).at 850° C., 0.4 s residence time, 16 g/h WHSV over 1.6 g of Na$_2$WO$_4$-promoted Mn$_2$O$_3$ supported on silica extrudate (Example 13) left) after 30 cycles and right) after 1600 cycles.

At 850° C., all four materials characterized in FIG. 13 under initial oxidative conditions comprise a spinel-type mixed magnesium manganese aluminum oxide as well as periclase (MgO). Platinum (from the heating stage) is also visible in several of the scans. Upon initial reduction (blue traces in FIG. 13), all samples in FIG. 13 undergo a reduction to form a mixed $Mg/Mn^{II}O$ as well as trace amounts of a spinel phase. The contribution of this spinel phase increases as the overall aluminum content in the support increases. The re-oxidation of the samples in FIG. 13 (orange traces) see a complete reversal of this transformation and the re-formation of the spinel-type magnesium manganese aluminum oxide.

What is of note is the shift in d-spacing of the (1 1 1) reflection of the spinel phase in the more aluminous, less magnesium-rich samples. In the 5:1 Mg:Al sample, we see little to no shift in the spinel phase after re-oxidation, while the 3:1 and the 7:6 samples shift markedly, indicative of the phases becoming more Mn-rich. Indeed, in the 7:6 sample, we can even observe two distinct reflections at 18° 2θ corresponding to different compositions on the spinel and a shift in intensity ratio of these two peaks that occurs concomitant to changes in the element distribution in the spinel phase. Like the re-oxidized samples in FIG. 13, the re-reduced samples also show similar changes. Observation of the (2 0 0) peak of the Mg/MnO phase shows that it shifts to smaller d-spacings upon cycling, which is the result of this phase becoming more Mg-rich. Like the change in composition of the spinel phase in the oxidized samples, the more aluminous samples show the greatest change in elemental ratio upon cycling. In addition to the this change in composition, the 7:6 Mg:Al sample also shows obvious grain ripening upon cycling. The 1:2 Mg:Al sample, in contrast, shows no discernable change in the PXRD patterns upon cycling; the only observable phase present in the sample, under both oxidizing and reducing conditions, is a magnesium manganese aluminum oxide.

Without being limited by theory, under the initial conditions under air, it would be expected that the manganese in the sample would adopt the manganese(III) oxidation state, and the presence of excess magnesium appears to lead the manganese(III) to assume the trivalent position in a spinel-type structure, $Mg(Al,Mn^{III})_2O_4$, while the excess magnesium in the sample takes the form of periclase (MgO), which accounts for the two phases that are observed in the PXRD patterns of the initial samples (other than the Pt heating stage). As observed by the in situ PXRD data, for the materials with 3:1 and 7:6 Mg:Al ratios, the spinel-type phase that is observable in the oxidizing steps appears to become enriched in manganese upon redox cycling, suggesting that magnesium is lost from the spinel structure and forms additional periclase (MgO). This trend suggests that after reducing treatment, redox-available manganese(III) in the form of $Mg(Al,Mn^{III})_2O_4$ is reduced to manganese(II), which results in the significant decrease of observable spinel structure in the PXRD (more of the spinel is retained when there is a higher concentration of aluminum present in the sample). Some of this manganese(II) incorporates into the divalent position of the spinel, displacing some of the magnesium from the spinel structure and forming $(Mg,Mn^{II})_2(Al,Mn^{III})_2O_4$ (with the quantity of $Mn^{III}$ in the trivalent site decreasing and the quantity of $Mn^{III}$ in the divalent site increasing with each redox cycle). Concomitantly, the manganese magnesium oxide observable under the reducing step of each redox cycle becomes further enriched with magnesium with each cycle. While the manganese in manganese magnesium oxide appears to be redox-active and available to participate in the chemical looping process, once the manganese(II) adopts the divalent position in the spinel structure, this Mn(II) state appears to be inert to re-oxidation by air under these conditions, causing a buildup of inactive manganese(II) as the material is redox-cycled. Because this manganese(II) is no longer redox-active, this buildup of manganese(II) leads to loss of activity in the material with respect to its function as a chemical looping (or oxygen storage) material.

For the sample containing 5:1 Mg:Al, the large excess of magnesium appears to have the effect of largely outcompeting manganese(II) from the divalent site of the magnesium manganese aluminum oxide, and as a result, the PXRD peaks do not significantly change with repeated redox cycling. This protection effect of the magnesium that preserves the activity of the manganese throughout cycling, preventing or at least slowing its deactivation, suggests that as the concentration of magnesium in the sample increases, so does the sample's ability to retain oxygen capacity and activity after repeated cycling. This trend is indeed borne out in the data shown in Table 1, which presents oxygen capacities for each of these sodium tungstate-promoted manganese oxide materials supported on magnesium aluminates. As these data indicate, a greater concentration of magnesium leads to greater retention of oxygen capacity.

TABLE 1

Oxygen capacity of $Na_2WO_4$-promoted manganese oxide supported on magnesium aluminum oxide after 30 chemical looping cycles.

| Support (Mg:Al) | O/Mn |
|---|---|
| 5:1 | 0.47 |
| 3:1 | 0.38 |
| 7:6 | 0.28 |
| 1:2 | 0.17 |

Example 15—Reactor Tests

Reactor Test Protocol

Catalysts were tested in a fixed bed quartz reactor with 8 mm inner diameter. An electric furnace maintained about 6 inches of the reactor at a temperature at 850° C. (FIG. S13). Catalysts were diluted with quartz powder and loaded in the bottom 3 inches of the hot zone of the reactor. Quartz powder was loaded in the top 3 inches of the reactor. Catalysts were supported on a quartz frit melted to the reactor wall to maintain their position. An oxidation-reaction cycle was performed by first flowing 200 sccm of 10% $O_2/N_2$ through the catalyst bed at 850° C. for 2 minutes. Then, the oxidizing gas was purged with argon flow of 200 sccm for 1 minute; with the geometry of the reactor with 13 mL of volume in the heated zone, this flow rate replaces 15 reactor volumes for thorough purging. The flow was then switched to a reactor bypass, and a flow of 200 sccm ethane was established. The ethane was switched to the reactor. Liquid water was trapped in a small dip leg, and the rest of the sample was collected using a 32-port Valco valve that trapped 15 samples in 1 mL loops. The samples were trapped at intervals between 2 and 30 seconds to capture the full transient response, with extra resolution at the beginning of the transient. After about 1 minute, ethane was purged with argon, and the cycle began again. The gas samples were analyzed in a gas chromatograph with Q and 5 Å molecular sieve columns feeding one thermal conductivity detector (TCD) using Ar carrier gas.

Data presented are from materials that have undergone at least 30 chemical looping cycles (ethane-purge-air-purge) unless otherwise specified. Without a loaded catalyst at 850° C., the micro-unit's effluent's composition is a good match for the yields for a conventional low residence time ethane steam cracker, which are 35% ethylene, 38% hydrogen, 18% ethane, and 6% methane on a mole basis. The micro-unit had fast transient response as shown by the rapid rise of the reaction products when the feed gas is switched from argon to ethane.

Reactor Test Results

Figure 1B:
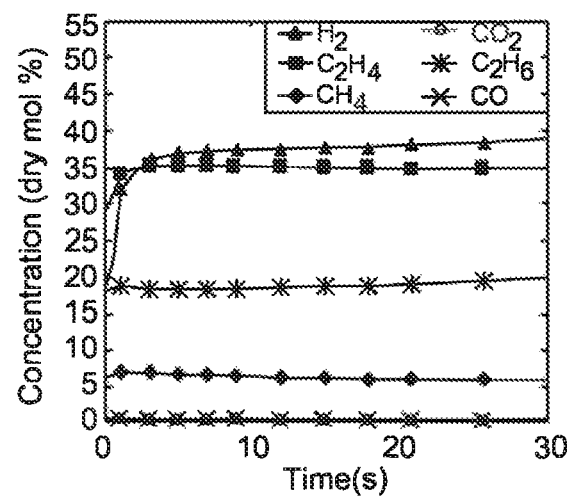
FIG. 1B is a graph showing the transient gaseous product composition from ethane feed gas at 850° C., 0.4 s residence time, 16 g/h WHSV, over 1.6 g of $Na_2WO_4$-promoted $Mn_2O_3$ supported on $\theta$-$Al_2O_3$ (Example 2).
Figure 2A:
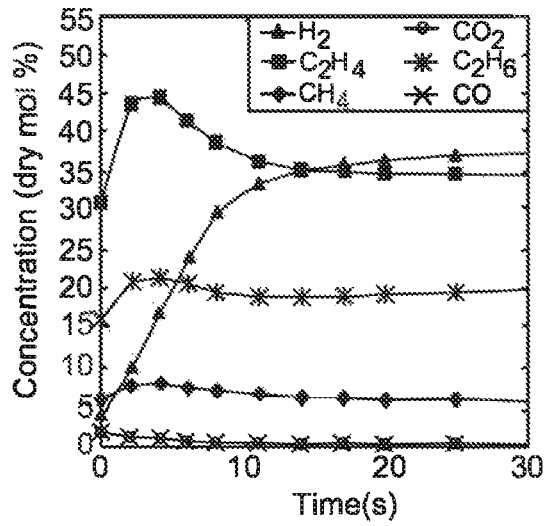
FIG. 2A is a graph showing the transient gaseous product composition from ethane feed gas at 850° C., 0.4 s residence time, 16 g/h WHSV, over 1.6 g of $Na_2WO_4$-promoted $Mn_2O_3$ supported on silica (Example 4).
Figure 2B:
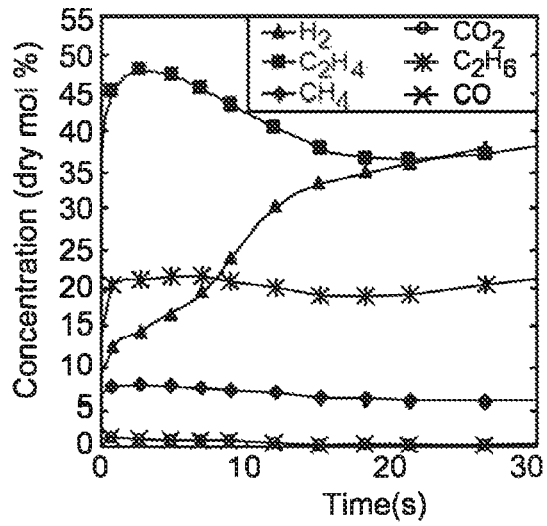
FIG. 2B is a graph showing the transient gaseous product composition from ethane feed gas at 850° C., 0.4 s residence time, 16 g/h WHSV, over 1.6 g of $Na_2WO_4$-promoted $Mn_2O_3$ supported on quartz (Example 6).
Figure 2C:
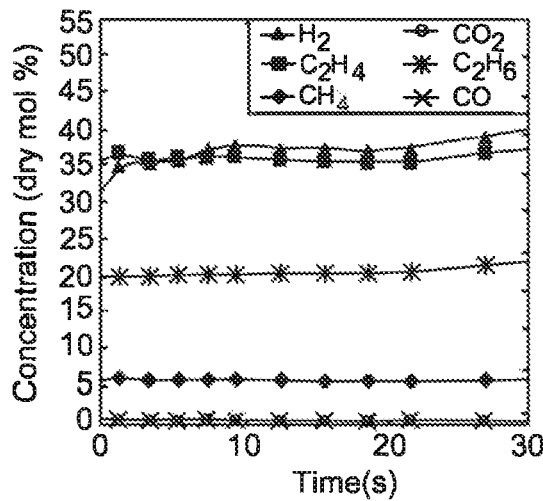
FIG. 2C is a graph showing the transient gaseous product composition from ethane feed gas at 850° C., 0.4 s residence time, 16 g/h WHSV, over 1.6 g of $Na_2WO_4$-promoted $Mn_2O_3$ supported on kaolinite (Example 3).
Figure 2D:
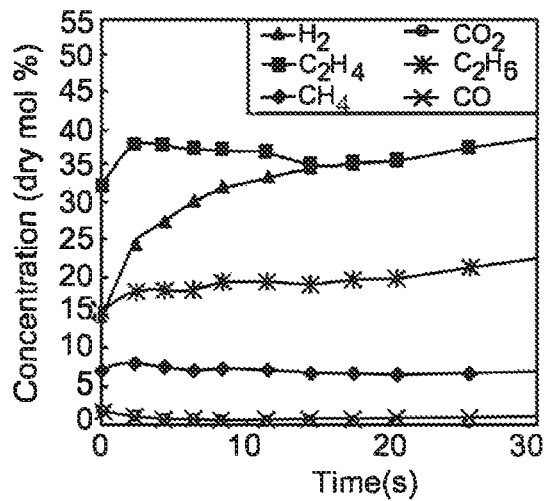
FIG. 2D is a graph showing the transient gaseous product composition from ethane feed gas at 850° C., 0.4 s residence time, 16 g/h WHSV, over 1.6 g of $Na_2WO_4$-promoted $Mn_2O_3$ supported on cordierite (Example 8).

FIG. 1. Examples 1, 2

Examples 1 and 2 are not effective for chemical looping. They show very little enhancement of the ethylene concentration in the dry product. This is ascribed to the deactivation of manganese by strong interaction with alumina.

FIG. 2. Examples 3, 4, 6, 8

Examples 4 and 6 are effective for chemical looping. They show an increased ethylene concentration in the dry reaction product due to $H_2$ oxidation to water (not plotted). Examples 3 and 8 are not effective for chemical looping because they show very little enhancement of the ethylene concentration in the dry product. This is ascribed to the deactivation of manganese by strong interaction with alumina FIG. 3. Examples 5, 7

Figure 3A:
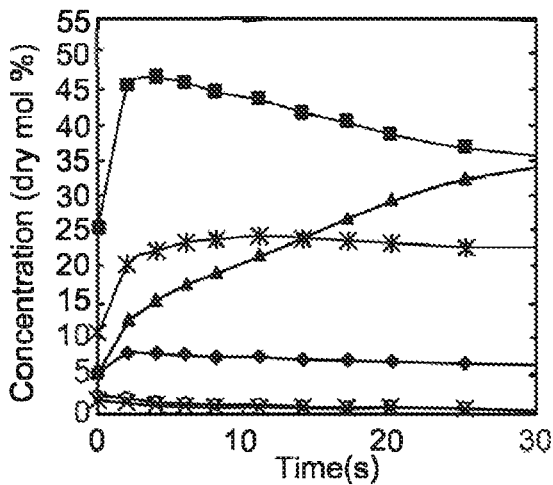
FIG. 3A is a graph showing the transient gaseous product composition from ethane feed gas at 850° C., 0.4 s residence time, 16 g/h WHSV over 1.6 g of $Na_2WO_4$-promoted $Mn_2O_3$ supported on magnesium silicate (Example 5) after 30 cycles.
Figure 3B:
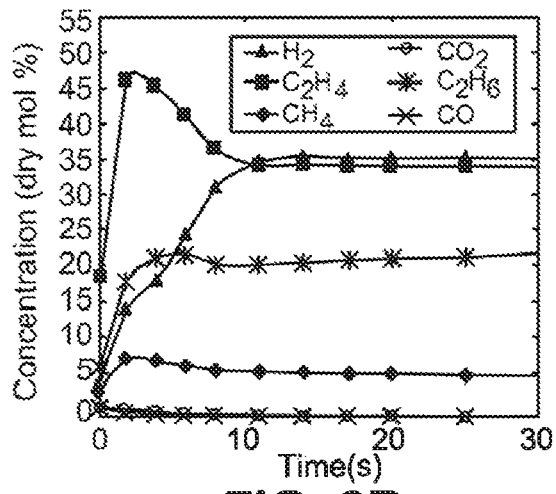
FIG. 3B is a graph showing the transient gaseous product composition from ethane feed gas at 850° C., 0.4 s residence time, 16 g/h WHSV over 1.6 g of $Na_2WO_4$-promoted $Mn_2O_3$ supported on magnesium silicate (Example 5) after 360 cycles.
Figure 3C:
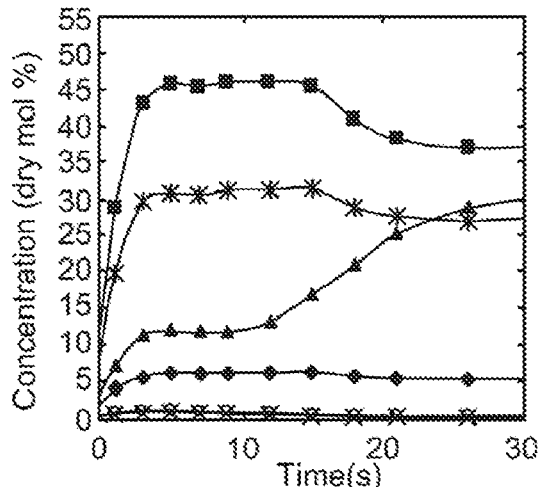
FIG. 3C is a graph showing the transient gaseous product composition from ethane feed gas at 850° C., 0.4 s residence time, 16 g/h WHSV over 1.6 g of $Na_2WO_4$-promoted $Mn_2O_3$ supported on magnesia (Example 7) after 30 cycles.
Figure 3D:
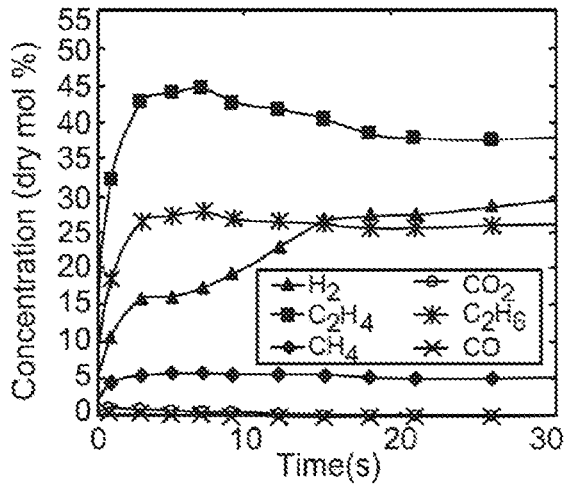
FIG. 3D is a graph showing the transient gaseous product composition from ethane feed gas at 850° C., 0.4 s residence time, 16 g/h WHSV over 1.6 g of Na$_2$WO$_4$-promoted Mn$_2$O$_3$ supported on magnesia (Example 7) after 360 cycles.
Figure 4A:
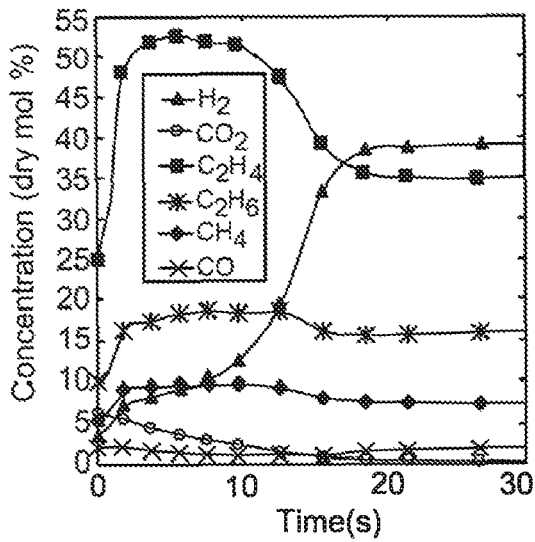
FIG. 4A is a graph showing the transient gaseous product composition from ethane feed gas at 850° C., 0.4 s residence time, 16 g/h WHSV over 1.6 g of Na$_2$WO$_4$-modified Mn$_2$O$_3$ supported on magnesium aluminate 5:1 Mg:Al (Example 11).
Figure 4B:
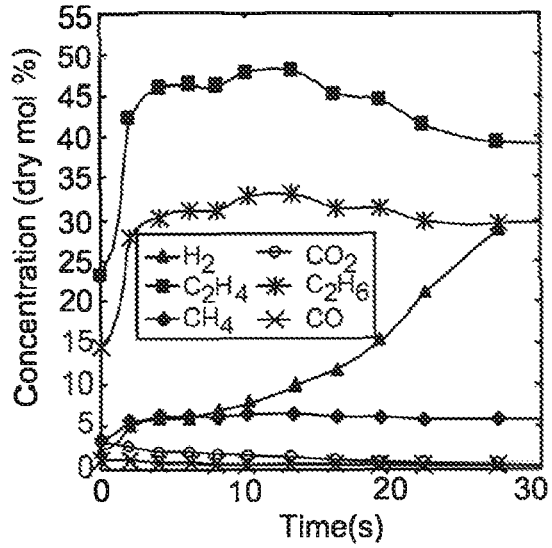
FIG. 4B is a graph showing the transient gaseous product composition from ethane feed gas at 850° C., 0.4 s residence time, 16 g/h WHSV over 1.6 g of Na$_2$WO$_4$-modified Mn$_2$O$_3$ supported on magnesium aluminate 3:1 Mg:Al (Example 12).
Figure 4C:
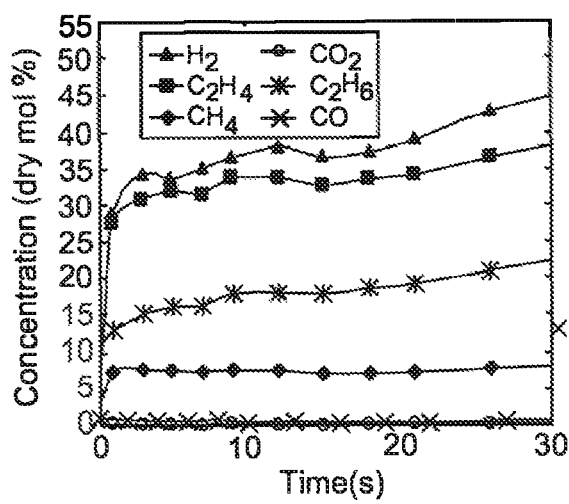
FIG. 4C is a graph showing the transient gaseous product composition from ethane feed gas at 850° C., 0.4 s residence time, 16 g/h WHSV over 1.6 g of Na$_2$WO$_4$-modified Mn$_2$O$_3$ supported on magnesium aluminate 1:2 Mg:Al [MgAl$_2$O$_4$] (Example 9).
Figure 4D:
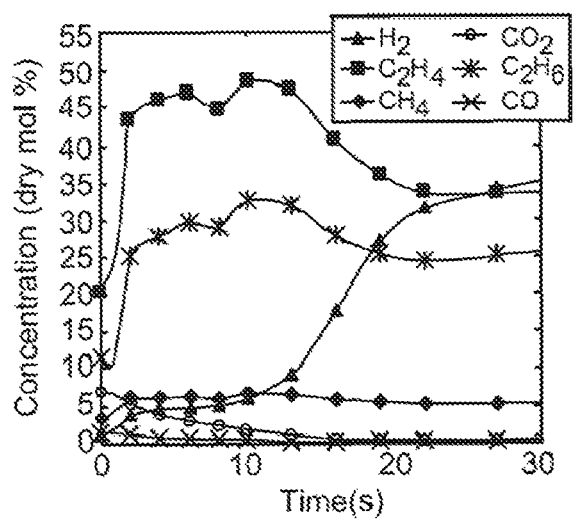
FIG. 4D is a graph showing the transient gaseous product composition from ethane feed gas at 850° C., 0.4 s residence time, 16 g/h WHSV over 1.6 g of Na$_2$WO$_4$-modified Mn$_2$O$_3$ supported on magnesium aluminate MG70 (Example 10).

Examples 5 and 7 are effective for chemical looping (FIG. 3a, 3c). They show enhancement of the ethylene concentration in the dry product. However, these materials lose effectiveness after extended use (FIG. 3b, 3d), with more loss seen in Example 5.

FIG. 4. Examples 9, 10, 11, 12

Figure 5:
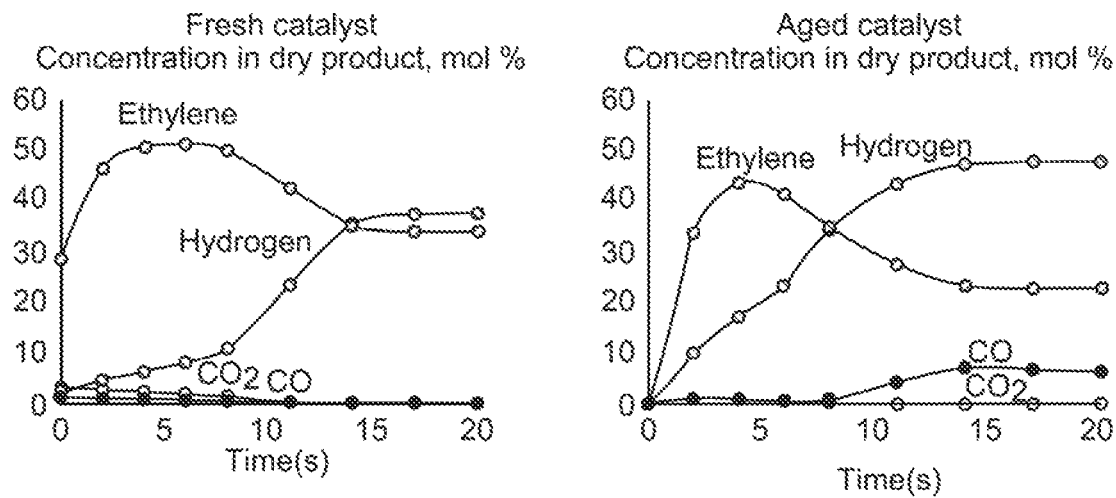
FIG. 5 is a graph showing transient gaseous product composition from ethane feed gas at 850° C., 0.4 s residence time, 16 g/h WHSV over 1.6 g of Na$_2$WO$_4$-promoted Mn$_2$O$_3$ supported on silica extrudate (Example 13) left) after 30 cycles and right) after 1600 cycles.
Figure 6:
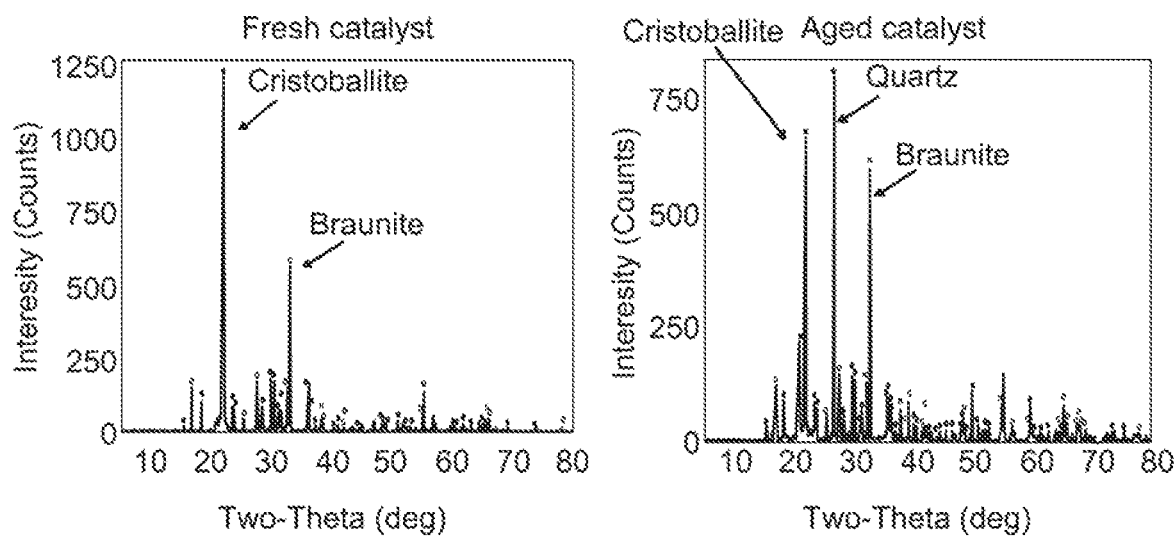
FIG. 6 is a powder X-ray diffraction pattern of Example 13 (left) fresh and (right) after 1600 cycles of chemical looping ethane conversion at 850° C.
Figure 7:
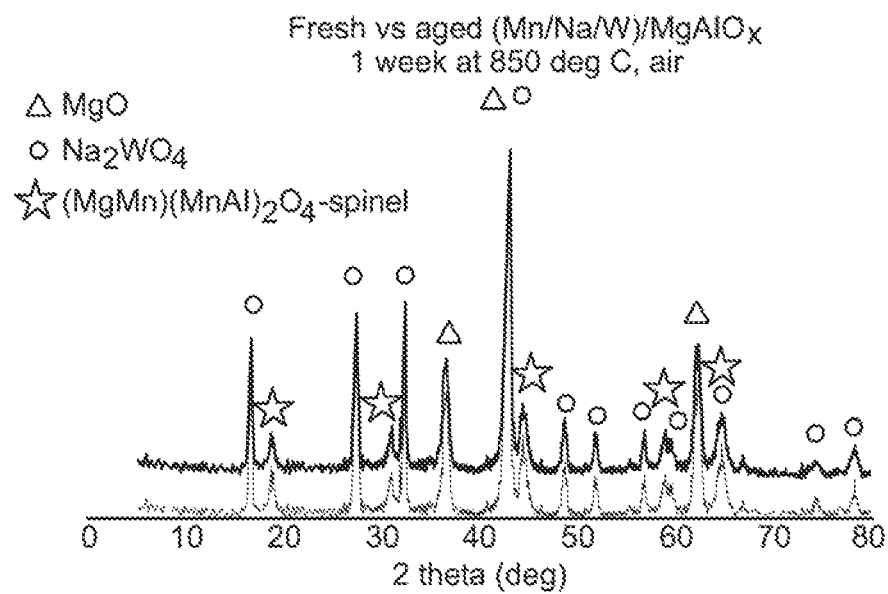
FIG. 7 is a powder X-ray diffraction pattern of Example 13 (upper) fresh and (lower) after 1600 cycles of chemical looping ethane conversion at 850° C.

Examples 10, 11, and 12 are effective for chemical looping (FIG. 5). They show enhancement in the ethylene concentration in the dry product. Example 9 is not effective for chemical looping. This is ascribed to the formation of manganese-aluminum mixed oxides which are inactive. This result shows the importance of having a Mg/Al ratio in the support in excess of 1:2. The preferred ratio of Mg/Al is closer to 3:1.

FIG. 5. Example 13

Example 13 is effective for chemical looping (FIG. 4,left). It shows enhancement in the ethylene concentration in the dry product. However, this material loses effectiveness after extended use (FIG. 4, right).

FIG. 6. Example 13

PXRD was used to investigate why Example 13 deactivated. The fresh material has several dominant crystal phases. Silica is mainly in the cristobalite phase. Sodium tungstate is present as a separate salt. Manganese is present mainly in the braunite and huebnerite phases. The braunite phase is ascribed as the active phase, due to the presence of Manganese in the 3+ oxidation state. The aged sample maintains braunite as the dominant manganese phase. However, the silica phase transforms to denser quartz. Therefore, the deactivation is associated with the densification of the support which occludes active manganese oxide.

FIG. 7. Example 12

PXRD was used to investigate the effects of aging on the Mn/Na/W catalyst supported on MgO-$Al_2O_3$ (Example 13). The fresh material has several dominant crystal phases. Sodium tungstate is present as a separate salt. Manganese and alumina are present only in the spinel phase along with Mg. Mn occupies both sites with 2+ and 3+ oxidation state. Additional Mg is present in an MgO phase (periclase). The aged sample maintains all species in the same crystal phases, unlike the material with SiO2 support. Moreover, the surface area of the aged inventive sample (Example 12) maintains higher surface area than the aged comparative sample (Example 13), as seen in Table 2.

TABLE 2

| BET surface area of Example 12 and 13 before and after aging at 850 deg C. in air for 1 week | | |
|---|---|---|
| Support | $SiO_2$ | $MgAl_2O_4$ |
| Fresh surf area | 45 m$^2$/g | 12 m$^2$/g |
| Aged surf area | 1.7 m$^2$/g | 7 m$^2$/g |

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired products, additional ingredients may be added, and/or similar ingredients may be substituted for one or more of the ingredients described.

Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. An active material, comprising:
   an active phase comprising an oxide of manganese and an alkali tungstate, wherein the oxide of manganese is reversibly oxidizable and/or reducible between oxidized and reduced states, wherein the oxide of manganese is present in the oxidized state, the reduced state, or a combination thereof; and
   a support phase comprising a) magnesia and alumina, b) magnesium aluminate, or c) a combination thereof.

2. The active material according to claim 1, wherein the ratio of magnesium to aluminum in the support phase is from about 10:1 to about 3:1.

3. The active metal material according to claim 2, wherein the ratio of magnesium to aluminum in the support phase is from about 7:1 to about 3:1.

4. The active metal material according to claim 3, wherein the ratio of magnesium to aluminum in the support phase is from about 5:1 to about 3:1.

5. The active material according to claim 1, wherein the oxidized state of the oxide of manganese comprises a spinel structure.

6. The active material of claim 1, wherein the alkali tungstate in the active phase comprises from 5 to 20 weight percent, based on the total weight of the active phase.

7. The active material of claim 1, wherein the alkali tungstate in the active phase comprises from 7 to 12 weight percent, based on the total weight of the active phase.

8. The active material according to claim 1, wherein the active phase further comprises a selectivity modifier.

9. The active material according to claim 1, wherein the active phase comprises from 1 to 20 percent by weight, based on the total weight of the active material.

10. The active material according to claim 9, wherein the active phase comprises from 4 to 15 percent by weight, based on the total weight of the active material.

11. The active material according to claim 10, wherein the active phase comprises from 5 to 10 percent by weight, based on the total weight of the active material.

12. The active material according to claim 1, wherein the alkali tungstate comprises sodium tungstate.

13. A reactor comprising the active material according to claim 1 disposed in a chemical looping reactor enclosure.

14. A method for making the active material according to claim 1, comprising the steps of:
   providing a substrate comprising the support phase; and
   coating the substrate with the active phase.

15. The method of claim 14, further comprising doping the active phase with a promoter.

16. The method of claim 15, wherein the active phase comprises manganese oxide and sodium tungstate.

17. A regenerative reaction process, comprising the sequential steps of:
   (a) disposing the active material according to claim 1 into a reactor member;
   (b) for a first period of time, contacting the oxidized state of the active phase of the active material in the reactor member with an oxidizable reactant at pressure, temperature, and flow rate conditions to reduce the active phase to the reduced state and form a reaction product;
   (c) for a second period of time, contacting the reduced state of the active phase of the active material in the reactor member with an oxidant to regenerate the active phase to the oxidized state for reduction in step (b); and
   (d) sequentially repeating steps (b) and (c) in the same reactor one or more times.

* * * * *